United States Patent [19]

Paques

[11] Patent Number: 5,156,967
[45] Date of Patent: Oct. 20, 1992

[54] PROCESS FOR THE PURIFICATION AND PASTEURIZATION OF UROKINASE

[75] Inventor: Eric Paques, Marburg, Fed. Rep. of Germany

[73] Assignee: Hoechst Aktiengesellschaft, Frankfurt am Main, Fed. Rep. of Germany

[21] Appl. No.: 590,557

[22] Filed: Sep. 28, 1990

Related U.S. Application Data

[63] Continuation of Ser. No. 293,561, Jan. 3, 1989, abandoned, which is a continuation of Ser. No. 793,315, Oct. 31, 1985, abandoned.

[30] Foreign Application Priority Data

Nov. 2, 1984 [DE] Fed. Rep. of Germany ....... 3439980

[51] Int. Cl.$^5$ ................. C12N 9/72; C12N 7/04
[52] U.S. Cl. ........................ 435/215; 435/236; 424/94.63
[58] Field of Search .............. 435/215, 814, 815, 217, 435/236; 424/94, 63

[56] References Cited

U.S. PATENT DOCUMENTS

| | | | |
|---|---|---|---|
| 3,184,394 | 5/1965 | Schmidtberger et al. | 435/216 X |
| 4,066,506 | 1/1978 | Johnson et al. | 195/66 B |
| 4,169,764 | 10/1979 | Takezawa et al. | 435/215 |
| 4,189,350 | 2/1980 | Yanagi et al. | 435/215 |
| 4,286,063 | 8/1981 | Suyama | 435/215 |

FOREIGN PATENT DOCUMENTS

1068817 5/1967 United Kingdom.

OTHER PUBLICATIONS

Nobuhara et al., "A Comparative Study of High Molecular Weight Urokinase and Low Molecular Weight Urokinase," J. Biochem 90: 225-223 (1981).
Barlow et al., "On The Conversion of High Molecular Weight Urokinase to the Low Molecular Weight Form By Plasmin," Thrombosis Research 23:541-547 (1981).
Ion Exchange Chromatography (1982) Published by Pharmecia Fine Chemicals, pp. 43-47.
Eisenberg & Crothers, Physical Chemistry, Benjamin Cumming Co., Inc. 1979, p. 344.
Xia, J., et al. (1983) Chem. Abst., 98:139495g.
Su, Y-C, et al. (1980) Chem. Abst., 93:64295c.
Liu, L. (1982) Chem. Abst. 96:195614r.
Kol'tsova, S. V., et al. (1981) Chem. Abst. 95:182914t.
Si., S., et al. (1986) Chem. Abst. 104:135917r.
Kirin University (1980) Chem. Abst. 93:21364g.
Methods in Enzymology vol. 22, p. 285 (1971).

*Primary Examiner*—Charles L. Patterson, Jr.
*Attorney, Agent, or Firm*—Finnegan, Henderson, Farabow, Garrett and Dunner.

[57] ABSTRACT

A process for the purification and pasteurization of urokinase using an ion exchanger is described, the product obtained having a favorable ratio of high molecular weight to low molecular weight urokinase. The product can be used for therapeutic purposes.

5 Claims, No Drawings

PROCESS FOR THE PURIFICATION AND PASTEURIZATION OF UROKINASE

This application is a continuation of application Ser. No. 07/293,561 filed Jan. 3, 1989, which is a continuation of application Ser. No. 06/793,315 filed Oct. 31, 1985.

The invention relates to a process for the purification and pasteurization of urokinase. Urokinase obtained by this process can be used as a thrombolytic.

Plasminogen is converted into plasmin under the influence of catalysts. Urokinase is one of the catalysts of this reaction. Urokinase is found, for example, in traces in human urine. The use of urokinase for thrombolysis is known. It is also already known that the commercially available urokinase products are frequently composed of a mixture of a high (54,000 M.W.) and a low (33,000 M.W.) molecular weight form of urokinase. The high molecular weight urokinase (HMW-UK) corresponds to the natural form of the molecule, whereas the low molecular weight form (LMW-UK) represents a product of proteolytic degradation of HMW-UK.

HMW-UK is preferred for therapeutic administration because it corresponds to the natural form. It is unclear whether the conversion into the low molecular weight form is brought about by autocatalysis or by contaminating proteases (J. Biochem. 90 (225-232) 1981; Thromb. Res. 23 (541-547) 1981).

Various methods for the isolation and purification of urokinase have already been described. These processes lead mainly to the preparation of urokinase products which have an unfavorable ration of HMW to LMW-UK.

A method for obtaining HMW-urokinase is described in German Offenlegungsschrift 2,815,853. The yield when this process is used is very low, caused by the removal of the LMW fractions, as well as because the degradation of the HMW-urokinase is not prevented.

The present invention has the object of producing a urokinase preparation which has a high proportion of HMW-urokinase, as is found in urine, and high stability.

It has been found, surprisingly, that it is possible to separate urokinase in good yield from concomitant proteins by binding the urokinase from a solution onto a cation exchanger and carrying out stepped gradient elution, and this purification process considerably increases the stability of the HMW-urokinase. It has also been found, suprisingly, that the degradation of the HMW-urokinase during a heat treatment to inactivate viruses can be prevented by dilution of the urokinase solution to a concentration of 10,000 to 100,000 IU/ml, or by adjustment to a pH of less than 6, preferably of 4 to 5.95.

It is possible to combine these three procedures.

Thus the invention relates to a process for the purification of urokinase, in which foreign substances having proteolytic activity are removed, which process makes it possible to prepare a product of high stability in good yield.

The invention also relates to a process for the pasteurization of a solution of urokinase without a considerable reduction in the proportion of HMW-UK and in the urokinase activity.

The invention particularly relates to a process for the purification of urokinase, which comprises bringing a solution of urokinase into contact with a cation exchanger, removing impurities having proteolytic activity from the loaded exchanger by stepped elution, and eluting the urokinase.

It is possible, for example, to use urine as the starting solution.

The invention also relates to a process for the inactivation of pathogenic viruses in a solution of urokinase by heat treatment, which comprises the solution of urokinase being adjusted to a pH of less than 6, preferably of 4 to 5.95, and to a urokinase concentration of 10,000 to 100,000 IU/ml and then being heated in the presence of a monosaccharide or disaccharide or sugar alcohol and, where appropriate, an aminoacid, at a temperature of 40°–90° C., preferably 55°–65° C., for at least 1 hour, preferably 8 to 20 hours. The solution of urokinase can then be concentrated and sterilized by filtration. The concentration of the saccharide is preferably 400–600 g/l, and that of the aminoacid 1–3 mol/l.

The invention also relates to the use of a product prepared in this manner for therapeutic purposes, which product can be administered by, in particular, injection, perfusion or in analogous ways.

If the urokinase-containing aqueous solution contains interfering quantities of salts, these are advantageously removed from it to a substantial extent.

Other concomitant undesired proteins can, where appropriate, be removed using, for example, an anion exchanger.

A preferred process comprises the removal, where appropriate, of salts from the solution containing urokinase, where appropriate bringing the low-salt solution into contact with an anion exchanger and removing the exchanger, where appropriate adjusting the supernatant or, alternatively, the desalted solution to pH 5 to 6, preferably 5.4–5.6, and bringing it into contact with a cation exchanger, preferably CM-cellulose. The cation exchanger is washed with a buffer, preferably at pH 5.5, and preferably having a conductivity between 5 and 10 mSi (20° C.), and the urokinase is eluted with a buffer between pH 5.5 and 9.5, preferably between 6.5 and 9, and preferably having a conductivity between 20 and 30 mSi (20° C.).

In a particularly preferred embodiment, the process can be such that the solution containing urokinase, for example urine, is desalted where appropriate, impurities are removed where appropriate by treatment with an anion exchanger, the solution is adjusted to pH 5.5, and CM-cellulose is added and then removed and washed with a buffer, of pH 5.5, containing 0.07 mol/l sodium acetate and 0.5 mol/l glycine (conductivity: 0 to 5 mSi; 20° C.), then washed with a buffer containing 0.15 mol/l sodium acetate and 0.5 mol/l glycine, pH 5.5 (conductivity: 5 to 10 mSi; 20° C.), and then the urokinase is eluted with a buffer at pH 9 (conductivity: 20 to 30 mSi; 20° C.).

It is also possible to carry out the process such that the eluate is adjusted to a pH of 5.5 and, after addition of a monosaccharide or oligosaccharide or sugar alcohol, preferably 1 kg/l sucrose, and, where appropriate, of a watersoluble aminoacid, preferably 112 g/l glycine, and is heated at a final concentration between 10,000 and 100,000 IU/ml urokinase, preferably 50,000 IU/ml, at 60° C. for 10 hours, and is concentrated and sterilized by filtration.

A product prepared in the manner described is distinguished by having a HMW/LMW-urokinase ratio corresponding to the initial solution and having high purity with, at the same time, good stability.

When, for example, a starting material having a ratio of high molecular weight to low molecular weight urokinase of 70/30 was used, then the product obtained in a yield of 85% and a purity of more than 90% had the same ratio of HMW to LMW-UK. If the washing of the cation exchanger was omitted, the HMW/LMW ratio in the product was 55/45, the yield was 90% and the purity was less than 60%. In this case, the stability of the final product was also less. The polymer ratio shifted in favor of the low molecular weight fraction when a solution was allowed to stand at room temperature. The HMW/LMW-UK ratio has been determined by determination of the amidolytic activity after separation of the two forms on a mono-S column (FPLC-Pharmacia).

The yield and polymer ratio of the final product depend also on the pH during the heating step. It is advantageous for the pH to be about 5.5, at which a favorable ratio of high molecular weight to low molecular weight urokinase is obtained, with the yield being very good.

The invention is to be illustrated in detail by the example which follows.

EXAMPLE

1. Purification

Salt was removed from the urokinase-containing starting solution by gel filtration at 4° C., and the eluate was collected and impurities removed from it using DEAE-cellulose at pH 8. 300 g/l sucrose and 37.5 g/l glycine were added to the eluate, the pH was adjusted to 5.5 with hydrochloric acid, and, at 4° C., CM-cellulose which had been equilibrated with a solution containing 0.07 mol/l sodium acetate and 0.5 mole/l glycine and having a pH of 5.5 was added, and the mixture was stirred for 1 hour. The gel was sucked dry, washed with the equilibration buffer, packed into a column, and washed with a buffer containing 0.15 mol/l sodium acetate and 0.5 mol/l glycine, pH 5.5 (conductivity: 7.8-8.1 mSi, 20° C.), and then the urokinase was eluted with a solution containing 0.2 mol/l sodium acetate and 0.5 mol/l glycine, pH 9.0 (conductivity: 26-30 mSi, 20° C.).

2. Virus Inactivation 1 kg of sucrose and 112 g of glycine were added to each liter of the eluate, the pH was adjusted to 5.5 with hydrochloric acid, the concentration was diluted to 50,000 IU/ml urokinase, and then the solution was heated at 60° C. for 10 hours. The heated solution of urokinase was concentrated and then sterilized by filtration.

I claim:

1. A process for the inactivation of pathogens in a solution of urokinase comprising adjusting the concentration of urokinase in the solution to about 10,000 to 100,000 IU/ml and heating the solution in the presence of 0.4 to 1.0 kg/l sucrose and 1.0 to 3.0 mol/l glycine at a temperature of about 40° to 90° C. for at least one hour.

2. The process of claim 1, wherein said urokinase concentration is adjusted to about 50,000 IU/ml.

3. A process for the inactivation of pathogens in a solution of urokinase comprising adjusting the pH range of the solution of urokinase to less than 6.0, and heating the solution in the presence of 0.4 to 1.0 kg/l sucrose and 1.0 to 3.0 mol/l glycine at a temperature of about 40° to 90° C. for at least one hour, wherein said solution of urokinase is also adjusted to a urokinase concentration of about 10,000 to about 100,000 IU/ml.

4. The process according to claim 3, wherein said urokinase concentration is adjusted to about 50,000 IU/ml.

5. The process according to claim 4, wherein said solution of urokinase is adjusted to a pH of about 5.5.

* * * * *